United States Patent
Nalesnik

(10) Patent No.: US 8,017,805 B2
(45) Date of Patent: Sep. 13, 2011

(54) DIAROMATIC AMINES

(75) Inventor: Theodore E. Nalesnik, Hopewell Junction, NY (US)

(73) Assignee: Chemtura Corporation, Middle Bury, CT (US)

( * ) Notice: Subject to any disclaimer, the term of this patent is extended or adjusted under 35 U.S.C. 154(b) by 1373 days.

(21) Appl. No.: 11/546,449

(22) Filed: Oct. 10, 2006

(65) Prior Publication Data

US 2007/0082828 A1    Apr. 12, 2007

Related U.S. Application Data

(60) Provisional application No. 60/725,565, filed on Oct. 11, 2005.

(51) Int. Cl.
C07C 211/55    (2006.01)
C10M 133/12    (2006.01)

(52) U.S. Cl. ........ 564/305; 508/545; 508/556; 508/561; 508/563; 252/68

(58) Field of Classification Search .................. 564/305; 508/545; 252/68
See application file for complete search history.

(56) References Cited

U.S. PATENT DOCUMENTS

| | | | |
|---|---|---|---|
| 3,293,181 A | 12/1966 | Stuart | |
| 3,396,109 A | 8/1968 | Butler et al. | |
| 3,397,145 A | 8/1968 | Cyba | |
| 3,442,804 A | 5/1969 | Le Suer et al. | |
| 3,637,499 A | 1/1972 | Pollak | |
| 5,498,809 A | 3/1996 | Emert et al. | |
| 6,296,782 B1 * | 10/2001 | Schnur et al. | 252/68 |
| 2002/0065201 A1 * | 5/2002 | Ribeaud et al. | 508/375 |
| 2004/0099838 A1 * | 5/2004 | Leck et al. | 252/68 |
| 2006/0073992 A1 * | 4/2006 | Dong et al. | 508/422 |

OTHER PUBLICATIONS

Buu-Hoi, Ng. Ph; "Carcinogenic nitrogen compounds. XX. Benzacridines, benzocarbazoles and Benzophenarsazines with Hydrogenated Rings" Univ.Paris. Journal of the Chemical Society. Abstracts. At pp. 2593-2596 (1956).

Buu-Hoi, Ng. Ph. et al. "Carcinogenic Nitrogen Compounds. Part XX. Benzacridines, Benzocarbazoles, and Benzophenarsazines with Hydrogenated Rings", *Journal of the Chemical Society*, pp. 2593-2596 (1956).

* cited by examiner

*Primary Examiner* — Ellen McAvoy
(74) *Attorney, Agent, or Firm* — Joseph Suhadolnik

(57) ABSTRACT

Diaromatic amine compounds or an isomer or isomeric mixture thereof is provided having the general formula:

$$(R)_n \underset{R^1}{\diagup\!\!\!\diagdown}\!\!-\!\!\overset{H}{\underset{R^2\ R^4}{N}}\!\!-\!\!\underset{R^5}{\diagup\!\!\!\diagdown}(R^3)_m$$

wherein n, m, R, $R^1$, $R^2$, $R^3$, $R^4$ and $R^5$ are as defined herein are provided. Lubricating oil compositions and stabilizer-containing compositions containing the diaromatic amine compounds are also provided.

26 Claims, No Drawings

DIAROMATIC AMINES

PRIORITY

This application claims the benefit under 35 U.S.C. §119 to U.S. Provisional Application No. 60/725,565, filed on Oct. 11, 2005, and entitled "DIAROMATIC AMINE DERIVATIVES AS ANTIOXIDANT", the contents of which are incorporated by reference herein.

BACKGROUND OF THE INVENTION

1. Technical Field

The present invention generally relates to additives for stabilizing organic products that are subjected to oxidative, thermal, and/or light-induced degradation. More particularly, the present invention generally relates to a class of diaromatic amines.

2. Description of the Related Art

The stabilization of organic materials with antioxidants or other stabilizers are well known to those skilled in the art. For example, in developing lubricating oils, there have been many attempts to provide additives that impart, for example, antioxidant, antiwear, and deposit control properties thereto. Zinc dialkyldithiophosphates (ZDDP) have been used as antifatigue, antiwear, antioxidant, extreme pressure and friction modifying additives for lubricating oils for many years. However, they are subject to several drawbacks owing to their zinc and phosphorus contents. The presence of zinc contributes to the emission of particulates in the exhaust. In addition, during operation of an internal combustion engine, lubricating oil enters the combustion chambers by means such as clinging to cylinder walls as the piston makes its down stroke.

When phosphorus-containing lubricating oil compositions enter the combustion reaction, phosphorus enters the exhaust stream where it acts as a catalyst poison thus shortening the useful life of the catalytic converter. However, zinc dialkyldithiophosphates give rise to ash, which contributes to particulate matter in automotive exhaust emissions, and regulatory agencies are seeking to reduce emissions of zinc into the environment. In addition, phosphorus, also a component of ZDDP, is suspected of limiting the service life of the catalytic converters that are used on cars to reduce pollution. It is important to limit the particulate matter and pollution formed during engine use for toxicological and enviromental reasons, but it is also important to maintain undiminished the antioxidant properties of the lubricating oil.

In view of the aforementioned shortcomings of the known zinc and phosphorus-containing additives, efforts have been made to provide lubricating oil additives that contain neither zinc nor phosphorus or, at least, contain them in substantially reduced amounts.

Buu-Hoi, Ng. et al., "Journal of the Chemical Society" Abstracts, pp. 2593-6 (1956) disclose the 1,1-isomer of a ditetralin amine compound of the formula.

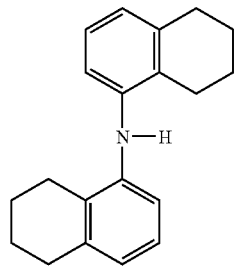

It would therefore be desirable to provide improved additives for stabilizing organic products that are subject to oxidative, thermal, and/or light-induced degradation and in need of stabilization to prevent or inhibit such degradation, e.g., additives for lubricating oils that can improve the antioxidant properties of the oil while reducing the content of zinc and phosphorous of the lubricating oils.

SUMMARY OF THE INVENTION

In accordance with one embodiment of the present invention, a diaromatic amine compound is provided having the general formula:

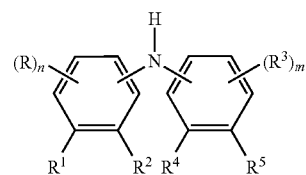

wherein n is from 0 to 3; m is from 0 to 3; each R and $R^3$ substituent is independently hydrogen, a straight or branched $C_1$-$C_{30}$ alkyl group or alkenyl group, substituted or unsubstituted $C_3$-$C_{12}$ cycloalkyl, substituted or unsubstituted $C_5$-$C_{12}$ aryl, hydroxyl-containing group, halogen, substituted or unsubstituted $C_1$-$C_{20}$ alkoxy, ester-containing group, ether-containing group, polyether-containing group, amide-containing group, or amine-containing group or two R substituents and/or two $R^3$ substituents together with the carbon atom to which they are bonded are joined together to form a substituted or unsubstituted, saturated, partially saturated or unsaturated $C_5$-$C_{30}$ ring structure optionally containing one or more heteroatoms; $R^1$ and $R^2$ together with the carbon atom to which they are bonded are joined together to form a substituted or unsubstituted, saturated or partially saturated $C_5$-$C_{30}$ ring structure optionally containing one or more heteroatoms, and $R^4$ and $R^5$ are independently hydrogen, a straight or branched $C_1$-$C_{30}$ alkyl group or alkenyl group, substituted or unsubstituted $C_3$-$C_{12}$ cycloalkyl, substituted or unsubstituted $C_5$-$C_{12}$ aryl, hydroxyl-containing group, halogen, substituted or unsubstituted $C_1$-$C_{20}$ alkoxy, ester-containing group, ether-containing group, polyether-containing group, amide-containing group, or amine-containing group or $R^4$ and $R^5$ together with the carbon atom to which they are bonded are joined together to form a substituted or unsubstituted, saturated or partially saturated $C_5$-$C_{30}$ ring structure optionally containing one or more heteroatoms or an isomer thereof and wherein the diaromatic amine compound is not a 1,1-isomer of a compound of the formula:

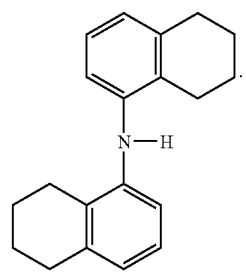

In accordance with a second embodiment of the present invention, a diaromatic amine compound is provided having the general formula:

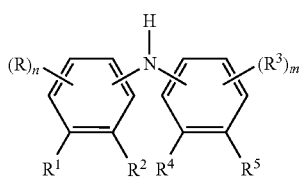

wherein n, m, R and $R^3$ have the aforementioned meanings; and $R^1$ and $R^2$ together with the carbon atoms to which they are bonded are joined together to form a substituted or unsubstituted, saturated or partially unsaturated, 5-, 6- or 7-membered ring optionally substituted with one or more heteroatoms and $R^4$ and $R^5$ are independently hydrogen, a straight or branched $C_1$-$C_{30}$ alkyl group or alkenyl group, substituted or unsubstituted $C_3$-$C_{12}$ cycloalkyl, substituted or unsubstituted $C_5$-$C_{12}$ aryl, hydroxyl-containing group, halogen, substituted or unsubstituted $C_1$-$C_{20}$ alkoxy, ester-containing group, ether-containing group, polyether-containing group, amide-containing group, or amine-containing group or $R^4$ and $R^5$ together with the carbon atoms to which they are bonded are joined together to form a substituted or unsubstituted, saturated or partially unsaturated, 5-, 6- or 7-membered ring optionally substituted with one or more heteroatoms or an isomer thereof and wherein the diaromatic amine compound is not a 1,1-isomer of a compound of the formula:

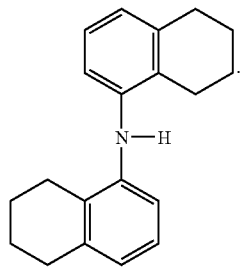

In accordance with a third embodiment of the present invention, a diaromatic amine compound is provided having the general formula:

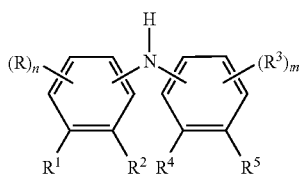

wherein n, m, R, $R^1$, $R^2$, $R^3$, $R^4$ and $R^5$ have the aforementioned meanings; wherein the diaromatic amine compound is a 1,2-isomer and/or 2,2-isomer or a mixture thereof.

In accordance with a fourth embodiment of the present invention, an isomeric mixture is provided comprising diaromatic amine compounds of the general formula:

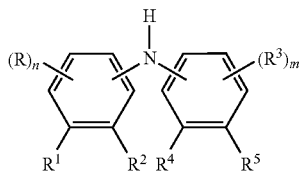

wherein n, m, R, $R^1$, $R^2$, $R^3$, $R^4$ and $R^5$ have the aforementioned meanings.

In accordance with a fourth embodiment of the present invention, an additive package comprising about 10 to about 75 weight percent of the foregoing diaromatic amine compounds or an isomer or isomeric mixture thereof.

In accordance with a fifth embodiment of the present invention, a lubricating oil composition is provided comprising (a) an oil of lubricating viscosity and (b) an antioxidant improving effective amount of at least one diaromatic amine compound of the general formula:

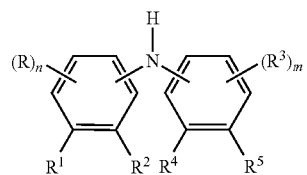

wherein n, m, R, $R^1$, $R^2$, $R^3$, $R^4$ and $R^5$ have the aforementioned meanings, or an isomer or isomeric mixture thereof.

In accordance with a sixth embodiment of the present invention, a stabilizer-containing composition is provided comprising (a) an organic material subject to oxidative, thermal, and/or light-induced degradation and in need of stabilization to prevent or inhibit such degradation; and (b) a stabilizing effective amount of at least one at least one diaromatic amine compound of the general formula:

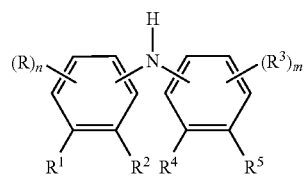

wherein n, m, R, $R^1$, $R^2$, $R^3$, $R^4$ and $R^5$ have the aforementioned meanings, or an isomer or isomeric mixture thereof.

In accordance with a seventh embodiment of the present invention a method for stabilizing an organic material subject to oxidative, thermal, and/or light-induced degradation and in need of stabilization to prevent or inhibit such degradation is provided, the method comprising adding to the organic material a stabilizing effective amount of at least one at least one diaromatic amine compound of the general formula:

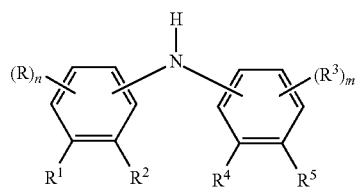

wherein n, m, R, $R^1$, $R^2$, $R^3$, $R^4$ and $R^5$ have the aforementioned meanings, or an isomer or isomeric mixture thereof.

The present invention advantageously provides diaromatic amine compound additives and lubricating oil compositions containing same which provide deposit protection in addition to oxidation-corrosion protection. The lubricating oil compositions can also provide such protection while having relatively low levels of phosphorous, i.e., less than about 0.1%, preferably less than about 0.08% and more preferably less than about 0.05% by weight. Accordingly, the lubricating oil compositions of the present invention can be more environmentally desirable than the higher phosphorous lubricating oil compositions generally used in internal combustion engines because they facilitate longer catalytic converter life and activity while also providing the desired high deposit protection. This is due to the substantial absence of additives containing phosphorus compounds in these lubricating oil compositions. The diaromatic amine derivative additives of this invention may also protect against oxidation both in the presence of transition metals such as, for example, iron (Fe) and Copper (Cu), etc., as well as in a metal free environment.

DETAILED DESCRIPTION OF THE PREFERRED EMBODIMENTS

The diaromatic amine compounds, isomers and isomeric mixtures thereof of the present invention are represented by general formula I:

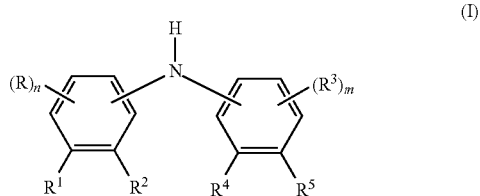

wherein n is from 0 to 3; m is from 0 to 3; each R and $R^3$ substituent is independently hydrogen, a straight or branched $C_1$-$C_{32}$ alkyl group or alkenyl group, substituted or unsubstituted $C_3$-$C_{12}$ cycloalkyl, substituted or unsubstituted $C_5$-$C_{12}$ aryl, hydroxyl-containing group, halogen, substituted or unsubstituted $C_1$-$C_{20}$ alkoxy, ester-containing group, ether-containing group, polyether-containing group, amide-containing group, or amine-containing group or two R substituents and/or two $R^3$ substituents together with the carbon atom to which they are bonded are joined together to form a substituted or unsubstituted, saturated, partially saturated or unsaturated $C_5$-$C_{30}$ ring structure optionally containing one or more heteroatoms; $R^1$ and $R^2$ together with the carbon atom to which they are bonded are joined together to form a substituted or unsubstituted, saturated or partially saturated $C_5$-$C_{30}$ ring structure optionally containing one or more heteroatoms, and $R^4$ and $R^5$ are independently hydrogen, a straight or branched $C_1$-$C_{30}$ alkyl group or alkenyl group, substituted or unsubstituted $C_3$-$C_{12}$ cycloalkyl, substituted or unsubstituted $C_5$-$C_{12}$ aryl, hydroxyl-containing group, halogen, substituted or unsubstituted $C_1$-$C_{20}$ alkoxy, ester-containing group, ether-containing group, polyether-containing group, amide-containing group, or amine-containing group or $R^4$ and $R^5$ together with the carbon atom to which they are bonded are joined together to form a substituted or unsubstituted, saturated or partially saturated $C_5$-$C_{30}$ ring structure optionally containing one or more heteroatoms.

Representative examples of alkyl groups for use herein include, by way of example, a straight or branched hydrocarbon chain radical containing carbon and hydrogen atoms of from 1 to about 18 carbon atoms with or without unsaturation, to the rest of the molecule, e.g., methyl, ethyl, n-propyl, 1-methylethyl (isopropyl), n-butyl, n-pentyl, etc., and the like.

Representative examples of halogens for use herein include, by way of example, chlorine, bromine, iodine, and the like.

Representative examples of hydroxyl-containing groups for use herein include, by way of example, —OH, a straight or branched hydrocarbon chain radical containing one or more hydroxyl groups bonded to a carbon atom on the hydrocarbon chain, and the like.

Representative examples of ester-containing groups for use herein include, by way of example, a carboxylic acid ester having one to 20 carbon atoms and the like.

Representative examples of ether or polyether containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are as defined herein, e.g., alkylene oxides, poly(alkylene oxide)s such as ethylene oxide, propylene oxide, butylene oxide, poly(ethylene oxide)s, poly(ethylene glycol)s, poly(propylene oxide)s, poly(butylene oxide)s and mixtures or copolymers thereof, an ether or polyether group of the general formula —$R_{20}OR_{21}$, wherein $R_{20}$ is a bond, an alkyl, cycloalkyl or aryl group as defined herein and $R_{21}$ is an alkyl, cycloalkyl or aryl group as defined herein and the like.

Representative examples of amide-containing groups for use herein include, by way of example, an amide of the general formula —$R_{23}C(O)NR_{24}R_{25}$ wherein $R_{23}$ can be a $C_1$-$C_{30}$ hydrocarbon, e.g., $R_{23}$ can be an alkylene group, arylene group, cycloalkylene group, and $R_{24}$ and $R_{25}$ can be $R_{24}$ and $R_{25}$ independently hydrogen or a $C_1$-$C_{30}$ hydrocarbon and the like.

Representative examples of amine-containing groups for use herein include, by way of example, an amine of the general formula —$R_{26}NR_{27}R_{28}$ wherein $R_{26}$ is a $C_2$-$C_{30}$ alkylene, arylene, or cycloalkylene and $R_{27}$ and $R_{28}$ are independently hydrogen or a $C_1$-$C_{30}$ hydrocarbon such as, for example, alkyl groups, aryl groups, or cycloalkyl groups as defined herein, and the like.

Representative examples of alkoxy groups for use herein include, by way of example, an alkyl group as defined above attached via oxygen linkage to the rest of the molecule, i.e., of the general formula —$OR_{29}$, wherein $R_{29}$ is an alkyl, cycloalkyl, cycloalkylalkyl, cycloalkenyl, aryl or an arylalkyl as defined above, e.g., —$OCH_3$, —$OC_2H_5$, or —$OC_6H_5$ which may be substituted or unsubstituted, and the like.

Representative examples of cycloalkyl groups for use herein include, by way of example, a substituted or unsubstituted non-aromatic mono or multicyclic ring system of about 3 to about 18 carbon atoms such as, for example, cyclopropyl, cyclobutyl, cyclopentyl, cyclohexyl, perhydronapthyl, adamantyl and norbornyl groups bridged cyclic group or spirobicyclic groups, e.g., sprio-(4,4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 3 to about 18 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 18 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 25 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined above directly bonded to an alkyl group as defined above, e.g., —$CH_2C_6H_5$, —$C_2H_5C_6H_5$ and the like, wherein the aryl group can optionally contain one or more heteroatoms, e.g., O and N, and the like.

Representative examples of heterocyclic ring groups for use herein include, by way of example, a substituted or unsubstituted stable 3 to about 15 membered ring radical, containing carbon atoms and from one to five heteroatoms, e.g., nitrogen, phosphorus, oxygen, sulfur and mixtures thereof. Suitable heterocyclic ring radicals for use herein may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, isochromanyl and the like and mixtures thereof.

Representative examples of heteroaryl groups for use herein include, by way of example, a substituted or unsubstituted heterocyclic ring radical as defined above. The heteroaryl ring radical may be attached to the main structure at any heteroatom or carbon atom that results in the creation of a stable structure.

Representative examples of heteroarylalkyl groups for use herein include, by way of example, a substituted or unsubstituted heteroaryl ring radical as defined above directly bonded to an alkyl group as defined above. The heteroarylalkyl radical may be attached to the main structure at any carbon atom from the alkyl group that results in the creation of a stable structure.

Representative examples of heterocyclo groups for use herein include, by way of example, a substituted or unsubstituted heterocyclic ring radical as defined above. The heterocyclo ring radical may be attached to the main structure at any heteroatom or carbon atom from the heterocyclo ring that results in the creation of a stable structure.

Representative examples of heterocycloalkyl groups for use herein include, by way of example, a substituted or unsubstituted heterocyclic ring radical as defined above directly bonded to an alkyl group as defined above. The heterocycloalkyl radical may be attached to the main structure at carbon atom in the alkyl group that results in the creation of a stable structure.

The substituents in the 'substituted alkyl', 'substituted alkoxy', 'substituted cycloalkyl', 'substituted cycloalkylalkyl', 'substituted cycloalkenyl', 'substituted arylalkyl', 'substituted aryl', 'substituted heterocyclic ring', 'substituted heteroaryl ring,' 'substituted heteroarylalkyl', 'substituted heterocycloalkyl ring', 'substituted cyclic ring' and 'substituted carboxylic acid derivative' may be the same or different and include one or more substituents such as hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocycloalkyl ring, substituted or unsubstituted heteroarylalkyl, substituted or unsubstituted heterocyclic ring, —COORx, —C(O)Rx, —C(S)Rx, —C(O)NRxRy, —C(O)ONRxRy, —NRxCONRyRz, —N(Rx)SORy, —N(Rx)SO2Ry, —(=N—N(Rx)Ry), —NRxC(O)ORy, —NRxRy, —NRxC(O)Ry-, —NRxC(S)Ry-NRxC(S)NRyRz, —SONRxRy-, —SO$_2$NRxRy-, —ORx, —ORxC(O)NRyRz, —ORxC(O)ORy-, —OC(O)Rx, —OC(O)NRxRy, —RxNRyC(O)Rz, —RxORy, —RxC(O)ORy, —RxC(O)NRyRz, —RxC(O)Rx, —RxOC(O)Ry, —SRx, —SORx, —SO$_2$Rx, —ONO2, wherein Rx, Ry and Rz in each of the above groups can be the same or different and can be a hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, 'substituted heterocycloalkyl ring' substituted or unsubstituted heteroarylalkyl, or a substituted or unsubstituted heterocyclic ring.

Representative examples of ring structures for $R^1$ and $R^2$ and $R^4$ and $R^5$ include independently, cycloalkyl, cycloalkenyl, heterocycloalkyl or heterocycloalkenyl as defined above, the ring structures being optionally substituted with one or more substituents. In one embodiment, each of $R^1$ and $R^2$ and $R^4$ and $R^5$ together with the carbon atom to which they are bonded are joined to form a cyclohexyl ring structure (to form a tetralin ring structure with the phenyl ring to which it is attached).

In one embodiment, a diaromatic amine compound of formula I is not a 1,1-isomer of a compound of the formula:

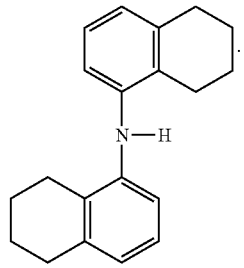

In one embodiment of the present invention, a diaromatic amine compound or an isomer or isomeric mixture thereof can be of the general formula:

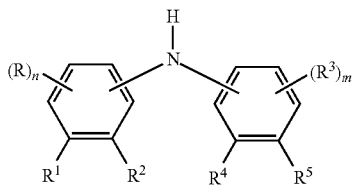

wherein n, m, R and $R^3$ have the aforementioned meanings; $R^1$ and $R^2$ together with the carbon atoms to which they are bonded are joined together to form a substituted or unsubstituted, saturated or partially unsaturated, 5-, 6- or 7-membered ring optionally substituted with one or more heteroatoms and $R^4$ and $R^5$ together with the carbon atoms to which they are bonded are joined together to form a substituted or unsubstituted, saturated or partially unsaturated, 5-, 6-, or 7-membered ring optionally substituted with one or more heteroatoms wherein the diaromatic amine is not a 1,1-isomer of the compound described above.

In another embodiment of the present invention, a diaromatic amine compound can be of the general formula:

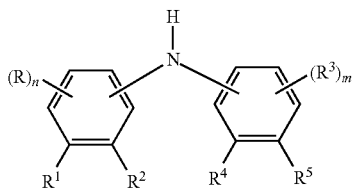

wherein n, m, R and $R^3$ have the aforementioned meanings; $R^1$ and $R^2$ together with the carbon atoms to which they are bonded are joined together to form a substituted or unsubstituted, saturated or partially unsaturated, 5-, 6-, or 7-membered ring optionally substituted with one or more heteroatoms and $R^4$ and $R^5$ together with the carbon atoms to which they are bonded are joined together to form a substituted or unsubstituted, saturated or partially unsaturated, 5-, 6-, or 7-membered ring optionally substituted with one or more heteroatoms, wherein the diaromatic amine compound is a 1,2-isomer or a 2,2-isomer or a mixture thereof.

Another embodiment is directed to an isomeric mixture of the diaromatic amine compounds of the present invention. In one embodiment, the isomeric mixture contains at least a 1,1-isomer, 1,2-isomer and a 2,2-isomer of the diaromatic amine compounds of the present invention. In another embodiment, the isomeric mixture contains at least a 1,1-isomer, 1,2-isomer and a 2,2-isomer of a diaromatic amine compound of the present invention wherein R and $R^3$ are each hydrogen; $R^1$ and $R^2$ together with the carbon atoms to which they are bonded are joined together to form a saturated or partially unsaturated 5-, 6-, or 7-membered ring and $R^4$ and $R^5$ together with the carbon atoms to which they are bonded are joined together to form a saturated or partially unsaturated 5-, 6-, or 7-membered ring. Generally, the isomeric mixtures can contain varying amounts of two or more of isomers of the diaromatic amine compounds of the present invention. For example, in one embodiment, the isomeric mixture can contain at least varying amounts of at least the 1,1-isomer and the 1,2-isomer. In another embodiment, the isomeric mixture can contain varying amounts of at least the 1,1-isomer and the 2,2-isomer. In another embodiment, the isomeric mixture can contain varying amounts of at least the 1,2-isomer and the 1,2-isomer. In another embodiment, the isomeric mixture can contain varying amounts of at least the 1,1-isomer, 1,2-isomer and the 2,2-isomer.

In one embodiment, the foregoing diaromatic amine compounds or an isomer or isomeric mixture thereof can be obtained by reacting an amino compound of general formula II:

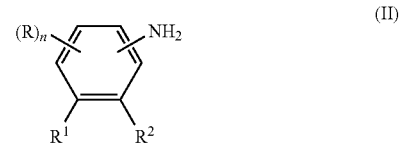

wherein n, R, $R^1$ and $R^2$ have the aforementioned meanings with a phenyl halide of general formula III

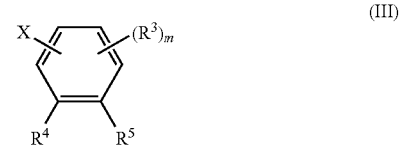

wherein m, $R^3$, $R^4$ and $R^5$ have the aforementioned meanings and X is a halide.

Alternatively, the foregoing diaromatic amine compounds or an isomer or isomeric mixture thereof can be obtained by reacting a phenyl halide of general formula IV:

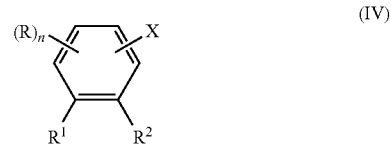

wherein n, R, $R^1$ and $R^2$ have the aforementioned meanings and X is a halide with an amino compound of general formula V:

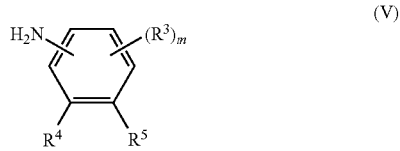

wherein m, $R^3$, $R^4$ and $R^5$ have the aforementioned meanings. Useful halides include, but are not limited to, bromine, chlorine, iodine, fluorine, etc., with bromine being preferred.

The diaromatic amine compounds or an isomer or isomeric mixture thereof of this invention can be obtained by reacting (1) the amino compound of the formula II and the phenyl halide of formula III, or (2) the phenyl halide of formula IV and the amino compound of formula V in the presence of a suitable catalyst. Useful catalysts include, but are not limited to, palladium-containing catalysts, copper-containing catalysts and the like and mixtures thereof. Suitable palladium-containing catalysts include, but are not limited to, tetrakis (triphenylphosphine)palladium, (dibenzylideneacetone) palladium, (dibenzylideneacetate)palladium, (tris (dibenzylideneacetate)dipalladium, bis (tricyclohexylphosphine)palladium, (2-(diphenylphosphino) ethyl)palladium, palladium(0) bis-(tri-t-butylphoshine), (1,1'-bis(diphenylphosphino)ferrocene)palladium, bis(triphenylphosphine)dichloropalladium, bis(1,1'-bis(diphenylphosphino)ferrocene)palladium, bis(2-(diphenylphosphino)ethyl)dichloropalladium, $PdCl_2$ $(CH_3CN)_2$ and the like. Suitable copper-containing catalysts include, but are not limited to, $Cu(PPh_3)_3Br$, $CuPPh_3$(phenantholine)Br, $CuPPh_3$ (1,10-dimethyl phenantholine)Br and the like. The catalyst can be present in an amount sufficient to promote the reaction. For example, in one embodiment, the copper-containing catalyst can be present in the reaction in an amount ordinarily ranging from about 15 to about 25 wt. %, based on the total weight of the reactants (with no solvent). In another embodiment, the palladium-containing catalyst can be present in the reaction in an amount ordinarily ranging from about 1 to about 3 wt. %, based on the total weight of the reactants (with no solvent).

The reaction is advantageously conducted under an inert gas atmosphere such as argon. The temperature for this reaction will ordinarily range from about 80° C. to about 150° C. and more preferably from about 100° C. to about 110° C. Generally, the molar ratio of the amino compound of the formula II to the phenyl halide of formula III can range from about 0.9:1 to about 1:0.9 and preferably from about 0.95:1 to about 1:0.95.

When forming a preferred ditetralin amine compound or an isomer or isomeric mixture thereof of this invention, a catalyst, e.g., $Cu(PPh_3)_3Br$, with a base, tetralin amine (e.g., of formula II) and a solvent, e.g., diethyl ethylene glycol, are charged into an argon flushed reaction vessel. The reaction material can be heated with stirring to a suitable temperature, e.g., about 110° C., for a suitable time, e.g., about 15 minutes, while maintained under an argon atmosphere. The reaction temperature can be lowered, e.g., to about 60° C., and a tetralin halide (e.g., of formula III) is then charged. The temperature is then raised, e.g., to about 110° C., and held for a suitable time, e.g., about 72 hours. The reaction is then cooled to, for example, about 60° C., and diluted with hexanes to precipitate out the salts which are removed by conventional techniques, e.g., filtration. If desired, the filtered solution can then be concentrated and placed on a preparative Silica-Gel column using, for example, hexanes, as the column solvent to isolate the ditetralin amine product.

In another embodiment, a diaromatic amine compound or an isomer or isomeric mixture thereof of this invention can be obtained by treating an amino compound of the formula II with a Lewis acid. Suitable Lewis acid catalysts include, but are not limited to iron halide $(FeX_n)$, titanium halide $(TiX_n)$, titanium alkoxide $(Ti(OR)_4)$, titanium oxide $(TiO_2)$, aluminum halide $(AlX_3)$, aluminum alkoxide $(Al(OR)_3)$, tin halide $(SnX_n)$, borone trihalide $(BX_3)$, magnesium halide $(MgX_2)$ and zinc halide $(ZnX_2)$. Alternatively, aluminum oxide may be used as a catalyst. The catalyst can be present in the reaction in an amount ordinarily ranging from about 0.1 to about 50% by weight and preferably from about 2 to 20% by weight, based on the weight of the reactants.

The catalyst can be used in the form of a fixed bed in the reactor or, for example, in the form of a fluidized bed and can have an appropriate shape. Suitable shapes include, for example, granules, pellets, monoliths, spheres or extrudates.

In this process of the present invention, it may not be necessary to use a reaction solvent. The reaction can be carried out at a temperature ranging from about 300° C. to about 550° C. and preferably from about 350° C. to about 400° C.

The diphenyl amine can be made in a process involving the nitration of benzene to nitrobenzene followed by reduction to aniline. This aniline intermediate is then sent through a fixed bed reactor, at elevated temperatures, containing a solid acidic catalyst which converts the aniline to diphenyl amine and ammonia. It is envisioned that ditetralin amine may be made in a similar process by substituting tetralin for benzene.

The diaromatic amine compounds or an isomer or isomeric mixture thereof of this invention may be used as a stabilizer in a stabilizer-containing composition containing an organic material subject to oxidative, thermal, and/or light-induced degradation and in need of stabilization to prevent or inhibit such degradation. Illustrative examples of such organic materials are as follows:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e., the polymers of monoolefins exemplified in the preceding paragraph, preferably polyethylene and polypropylene, and can be prepared by different, and especially by the following, methods: (a) radical polymerisation (normally under high pressure and at elevated temperature; or (b) catalytic polymerisation using a catalyst that normally contains one or more than one metal of Groups IVb, Vb, VIb or VIII of the Periodic Table. These metals usually have one or more than one ligand, typically oxides, halides, alcoholates, esters, ethers, amines, alkyls, alkenyls and/or aryls that may be either pi- or sigma-coordinated. These metal complexes may be in the free form or fixed on substrates, typically on activated magnesium chloride, titanium (III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of Groups Ia, IIa and/or IIIa of the Periodic Table. The activators may be modified conveniently with further ester, ether, amine or silyl ether groups. These catalyst systems are usually termed Phillips, Standard Oil Indiana, Ziegler (Natta), TNZ (DuPont), metallocene or single site catalysts (SSC).

2. Mixtures of the polymers mentioned under (1), for example, mixtures of polypropylene with polylsobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example, ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in (1) above, for example, polypropylene/ethylene-propylene copolymers, LDPE/ethylene-vinyl acetate copolymers (EVA), LDPE/ethylene-acrylic acid copolymers (EM), LLDPE/EVA, LLDPE/EAA and alternating or random polyalkylene/carbon monoxide copolymers and mixtures thereof with other polymers, for example, polyamides.

4. Hydrocarbon resins (for example $C_5$-$C_9$) including hydrogenated modifications thereof (e.g., tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(a-methylstyrene).

6. Aromatic homopolymers and copolymers derived from vinyl aromatic monomers including styrene, a-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including the aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, e.g., a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under (6), including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under (6a).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or a-methylstyrene, e.g., styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under (6), for example, the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example, polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from a,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under (9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in (1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example, polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example, poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g., with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example, polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g., products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose.

28. Blends of the aforementioned polymers (polyblends), for example, PP/EPDM, Polyamide/EPDM or ABS, PVC/EVA, PVC/ABS, PVC/MB S, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example, mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

Preferred organic materials are natural, semi-synthetic and synthetic polymers as described above. Representative examples of such organic materials for use herein include polyols, urethanes, reaction products of polyols and urethanes, plastics, greases, roof sheeting, motor oils, cables, gaskets, seals, rubber-containing compositions such as compounded tires, rubber belts, cables, gaskets, seals and rubber products in the garment and carpet industries.

The diaromatic amine compounds of the present invention can be added to the organic material in an amount sufficient to impart an appreciable stabilizing effect. In general, this amount may vary from about 0.1 wt. % to about 5 wt. %, preferably from about 0.5 wt. % to about 3 wt. % and more preferably from about 0.5 wt. % to about 2.0 wt. %, by total weight of the organic material. The diaromatic amine compounds can be incorporated into the organic material by conventional methods, for example, in any desired phase during the manufacture of shaped products. They can, for example, be mixed in the form of a liquid, a paste, a powder with other materials, suspensions or emulsions or solutions into the polymer, which can be in the form of a powder, melt, solution, suspension or emulsion.

Another embodiment of the present invention is a lubricating oil composition containing at least (a) an oil of lubricating viscosity and (b) an effective amount of at least one of the diaromatic amine compound or an isomer or isomeric mixture thereof of this invention. Generally, the oil of lubricating viscosity for use in the lubricating oil compositions may be present in a major amount, e.g., an amount of greater than 50 wt. %, preferably greater than about 70 wt. %, more preferably from about 80 to about 99.5 wt. % and most preferably from about 85 to about 98 wt. %, based on the total weight of the composition. The diaromatic amine compounds of this invention can be added to the lubricating oil composition in an effective amount ranging from about 0.1 wt. % to about 10 wt. %, preferably from about 0.5 wt. % to about 3 wt. % weight percent and more preferably from about 1 wt. % to about 2 wt. %, based on the total weight of the lubricating oil composition.

The oil of lubricating viscosity for use herein can be any presently known or later-discovered oil of lubricating viscosity used in formulating lubricating oil compositions for any and all such applications, e.g., engine oils, marine cylinder oils, functional fluids such as hydraulic oils, gear oils, transmission fluids, e.g., automatic transmission fluids, etc., turbine lubricants, compressor lubricants, metal-working lubricants, and other lubricating oil and grease compositions. Additionally, the oil of lubricating viscosity for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the oil of lubricating viscosity is dependent upon the application. Accordingly, the viscosity of an oil of lubricating viscosity for use herein will ordinarily range from about 2 to about 2000 centistokes (cSt) at 100° Centigrade (C.). Generally, individually the oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fisher-Tropsch process. For example, a suitable oil of lubricating viscosity is one that comprises little, if any, heavy fraction; e.g., little, if any, lube oil fraction of viscosity about 20 cSt or higher at 100° C.

The oil of lubricating viscosity may be derived from natural lubricating oils, synthetic lubricating oils or mixtures thereof. Suitable oils includes base stocks obtained by isomerization of synthetic wax and slack wax, as well as hydrocracked base stocks produced by hydrocracking (rather than solvent extracting) the aromatic and polar components of the crude. Suitable oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils includes, but is not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of about 1,000, diphenyl ether of polyethylene glycol having a molecular weight of about 500 to about 1000, diethyl ether of polypropylene glycol having a molecular weight of about 1,000 to about 1,500, etc.) or mono- and polycarboxylic esters thereof such as, for example, the acetic esters, mixed $C_3$-$C_8$ fatty acid esters, or the $C_{13}$oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The oil of lubricating viscosity may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The diaromatic amine compounds or an isomer or isomeric mixture thereof of this invention can be used as a complete or partial replacement for commercially available antioxidants currently used in lubricant formulations and can be in combination with other additives typically found in motor oils and fuels. When used in combination with other types of antioxidants or additives used in oil formulations, synergistic and/or additive performance effects may also be obtained with respect to improved antioxidancy, antiwear, frictional and detergency and high temperature engine deposit properties. Such other additives can be any presently known or later-discovered additives used in formulating lubricating oil compositions. The lubricating oil additives typically found in lubricating oils are, for example, dispersants, detergents, corrosion/rust inhibitors, antioxidants, anti-wear agents, anti-foamants, friction modifiers, seal swell agents, emulsifiers, VI improvers, pour point depressants, and the like. See, for example, U.S. Pat. No. 5,498,809 for a description of useful lubricating oil composition additives, the disclosure of which is incorporated herein by reference in its entirety.

Examples of dispersants include polyisobutylene succinimides, polyisobutylene succinate esters, Mannich Base ashless dispersants, and the like. Examples of detergents include metallic and ashless alkyl phenates, metallic and ashless sulfurized alkyl phenates, metallic and ashless alkyl sulfonates, metallic and ashless alkyl salicylates, metallic and ashless saligenin derivatives, and the like.

Examples of other antioxidants include alkylated diphenylamines, N-alkylated phenylenediamines, phenyl-naphthylamine, alkylated phenyl-naphthylamine, dimethyl quinolines, trimethyldihydroquinolines and oligomeric compositions derived therefrom, hindered phenolics, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds, and the like. Representative examples of such additives are those commercially available from such sources as Chemtura Corporation and include, for example, Naugalube® 438, Naugalube 438L, Naugalube 640, Naugalube 635, Naugalube 680, Naugalube AMS, Naugalube APAN, Naugard PANA, Naugalube TMQ, Naugalube 531, Naugalube 431, Naugard® BHT, Naugalube 403, Naugalube 420 and the like.

Examples of anti-wear additives that can be used in combination with the additives of the present invention include organo borates, organo phosphites, organo phosphates, organic sulfur-containing compounds, sulfurized olefins, sulfurized fatty acid derivatives (esters), chlorinated paraffins, zinc dialkyldithiophosphates, zinc diaryldithiophosphates, dialkyldithiophosphate esters, diaryl dithiophosphate esters, phosphosulfurized hydrocarbons, and the like. Representative examples of such additives are those commercially available from The Lubrizol Corporation such as Lubrizol 677A, Lubrizol 1095, Lubrizol 1097, Lubrizol 1360, Lubrizol 1395, Lubrizol 5139, Lubrizol 5604 and the like, and from Ciba Corporation such as Irgalube 353 and the like.

Examples of friction modifiers include fatty acid esters and amides, organo molybdenum compounds, molybdenum dialkyldithiocarbamates, molybdenum dialkyl dithiophosphates, molybdenum disulfide, tri-molybdenum cluster dialkyldithiocarbamates, non-sulfur molybdenum compounds and the like. Representative examples of such friction modifiers are those commercially available from R.T. Vanderbilt Company, Inc. such as Molyvan A, Molyvan L, Molyvan 807, Molyvan 856B, Molyvan 822, Molyvan 855, and the like; Asahi Denka Kogyo K.K. such as SAKURA-LUBE 100, SAKURA-LUBE 165, SAKURA-LUBE 300, SAKURA-LUBE 310G, SAKURA-LUBE 321, SAKURA-LUBE 474, SAKURA-LUBE 600, SAKURA-LUBE 700, and the like; and from Akzo Nobel Chemicals GmbH such as Ketjen-Ox 77M, Ketjen-Ox 77TS, and the like.

An example of an anti-foam agent is polysiloxane, and the like. Examples of rust inhibitors are polyoxyalkylene polyol, benzotriazole derivatives, and the like. Examples of VI improvers include olefin copolymers and dispersant olefin copolymers, and the like. An example of a pour point depressant is polymethacrylate, and the like.

As noted above, suitable anti-wear compounds include dihydrocarbyl dithiophosphates. Preferably, the hydrocarbyl groups contain an average of at least 3 carbon atoms. Particularly useful are metal salts of at least one dihydrocarbyl dithiophosphoric acid wherein the hydrocarbyl groups contain an average of at least 3 carbon atoms. The acids from which the dihydrocarbyl dithiophosphates can be derived can be illustrated by acids of the formula:

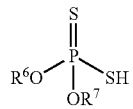

wherein $R^6$ and $R^7$ are the same or different and can be linear or branched alkyl, cycloalkyl, aralkyl, alkaryl, or substituted substantially hydrocarbyl radical derivatives of any of the above groups, and wherein the $R^6$ and $R^7$ groups in the acid each have, on average, at least 3 carbon atoms. By "substantially hydrocarbyl" is meant radicals containing substituent groups, e.g., 1 to 4 substituent groups per radical moiety such as, for example, ether, ester, thio, nitro, or halogen, that do not materially affect the hydrocarbon character of the radical.

Specific examples of suitable $R^6$ and $R^7$ radicals include isopropyl, isobutyl, n-butyl, sec-butyl, n-hexyl, heptyl, 2-ethylhexyl, diisobutyl, isooctyl, decyl, dodecyl, tetradecyl, hexadecyl, octadecyl, butylphenyl, o,p-dipentylphenyl, octylphenyl, polyisobutene-(molecular weight 350)-substituted phenyl, tetrapropylene-substituted phenyl, beta-octylbutyl-naphthyl, cyclopentyl, cyclohexyl, phenyl, chlorophenyl, o-dichlorophenyl, bromophenyl, naphthenyl, 2-methylcyclohexyl, benzyl, chlorobenzyl, chloropentyl, dichlorophenyl, nitrophenyl, dichlorodecyl and xenyl radicals. Alkyl radicals having from about 3 to about 30 carbon atoms and aryl radicals having from about 6 to about 30 carbon atoms are preferred. Particularly preferred $R^6$ and $R^7$ radicals are alkyl of from 4 to about 18 carbon atoms.

The phosphorodithioic acids are readily obtainable by the reaction of a phosphorus pentasulfide and an aliphatic alcohol and/or phenol. The reaction involves at least mixing, at a temperature ranging from about 20° C. to 200° C., about 4 moles of the alcohol or phenol with one mole of phosphorus pentasulfide. Hydrogen sulfide can be liberated as the reaction takes place. Mixtures of alcohols, phenols, or both can be employed, e.g., mixtures of $C_3$ to $C_{30}$ alcohols, $C_6$ to $C_{30}$ aromatic alcohols, etc. The metals useful to make the phosphate salts include, but are not limited to, Group I metals, Group II metals, aluminum, lead, tin, molybdenum, manganese, cobalt, and nickel with zinc being the preferred metal. Examples of metal compounds that can be reacted with the acid include lithium oxide, lithium hydroxide, lithium carbonate, lithium pentylate, sodium oxide, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum propylate, lead oxide, lead hydroxide, lead carbonate, tin oxide, tin butylate, cobalt oxide, cobalt hydroxide, cobalt carbonate, cobalt pentylate, nickel oxide, nickel hydroxide, nickel carbonate and the like and mixtures thereof.

In some instances, the incorporation of certain ingredients, particularly carboxylic acids or metal carboxylates, e.g., small amounts of the metal acetate or acetic acid, used in conjunction with the metal reactant will facilitate the reaction and result in an improved product. For example, the use of up to about 5% of zinc acetate in combination with the required amount of zinc oxide facilitates the formation of a zinc phosphorodithioate.

The preparation of metal phosphorodithioates is well known in the art. See, e.g., U.S. Pat. Nos. 3,293,181; 3,397,145; 3,396,109; and 3,442,804; the disclosures of which are hereby incorporated by reference. Also useful as anti-wear additives are amine derivatives of dithiophosphoric acid compounds, such as are described in U.S. Pat. No. 3,637,499, the disclosure of which is hereby incorporated by reference in its entirety.

The zinc salts are most commonly used as anti-wear additives in lubricating oils in amounts ranging from about 0.1 to about 10, preferably about 0.2 to about 2 wt. %, based upon the total weight of the lubricating oil composition. They may be prepared in accordance with known techniques, e.g., by first forming a dithiophosphoric acid, usually by reaction of an alcohol and/or a phenol with $P_2S_5$ and then neutralizing the dithiophosphoric acid with a suitable zinc compound.

Mixtures of alcohols can be used, including mixtures of primary and secondary alcohols, secondary generally for imparting improved antiwear properties and primary for thermal stability. In general, any basic or neutral zinc compound could be used, but the oxides, hydroxides, and carbonates are most generally employed. Commercial additives frequently contain an excess of zinc owing to use of an excess of the basic zinc compound in the neutralization reaction.

The zinc dihydrocarbyl dithiophosphates (ZDDP) are oil soluble salts of dihydrocarbyl esters of dithiophosphoric acids and can be represented by the following formula:

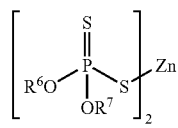

wherein $R^6$ and $R^7$ have the aforestated meanings.

The lubricating oil compositions of the present invention, when they contain these additives, are typically blended into a base oil in amounts such that the additives therein are effective to provide their normal attendant functions. Representative effective amounts of such additives are illustrated in Table 1.

TABLE 1

| Additives | Preferred Weight % | More Preferred Weight % |
|---|---|---|
| V.I. Improver | about 1 to about 12 | about 1 to about 4 |
| Corrosion Inhibitor | about 0.01 to about 3 | about 0.01 to about 1.5 |
| Oxidation Inhibitor | about 0.01 to about 5 | about 0.01 to about 1.5 |
| Dispersant | about 0.1 to about 10 | about 0.1 to about 5 |
| Lube Oil Flow Improver | about 0.01 to about 2 | about 0.01 to about 1.5 |
| Detergent/Rust Inhibitor | about 0.01 to about 6 | about 0.01 to about 3 |
| Pour Point Depressant | about 0.01 to about 1.5 | about 0.01 to about 0.5 |
| Anti-foaming Agents | about 0.001 to about 0.1 | about 0.001 to about 0.01 |
| Anti-wear Agents | about 0.001 to about 5 | about 0.001 to about 1.5 |
| Seal Swell Agents | about 0.1 to about 8 | about 0.1 to about 4 |
| Friction Modifiers | about 0.01 to about 3 | about 0.01 to about 1.5 |
| Lubricating Base Oil | Balance | Balance |

When other additives are employed, it may be desirable, although not necessary, to prepare additive concentrates comprising concentrated solutions or dispersions of the diaromatic amine additives of this invention (in concentrate amounts described herein), together with one or more other additives (the concentrate when constituting an additive mixture being referred to herein as an additive-package) whereby several additives can be added simultaneously to the base oil to form the lubricating oil composition. Dissolution of the additive concentrate into the lubricating oil can be facilitated by, for example, solvents and by mixing accompanied by mild heating, but this is not essential. The concentrate or additive-package will typically be formulated to contain the additives in proper amounts to provide the desired concentration in the final formulation when the additive-package is combined with a predetermined amount of base lubricant. Thus, the diaromatic amine additives of the present invention can be added to small amounts of base oil or other compatible solvents along with other desirable additives to form additive-packages containing active ingredients in collective amounts of, typically, from about 2.5 to about 90 percent, preferably from about 15 to about 75 percent, and more preferably from about 25 percent to about 60 percent by weight additives in the appropriate proportions with the remainder being base oil. The final formulations can typically employ about 1 to 20 weight percent of the additive-package with the remainder being base oil.

All of the weight percentages expressed herein (unless otherwise indicated) are based on the active ingredient (AI) content of the additive, and/or upon the total weight of any additive-package, or formulation, which will be the sum of the AI weight of each additive plus the weight of total oil or diluent.

In general, the lubricant compositions of the invention contain the additives in a concentration ranging from about 0.05 to about 30 weight percent. A concentration range for the additives ranging from about 0.1 to about 10 weight percent based on the total weight of the oil composition is preferred. A more preferred concentration range is from about 0.2 to about 5 weight percent. Oil concentrates of the additives can contain from about 1 to about 75 weight percent of the additive in a carrier or diluent oil of lubricating oil viscosity.

The following non-limiting examples are illustrative of the present invention.

EXAMPLE 1

Preparation of Ditetralin Amine Using Copper Coupling Catalyst

Into a warm dry 50 ml four neck reaction flask equipped with a mechanical stirrer, thermal couple, heating mantle, Argon blanket and septum injection port was charged Cu(PPh$_3$)$_3$Br (5.0 g) catalyst and potassium butoxide (4.5 gr). The vessel was now well flushed with argon gas and maintained under a dry argon blanket. Into the reaction vessel was injected a degassed 30 ml diethyl ethylene glycol solution containing tetralin amine (5.0 g).

The reaction mixture was heated, under argon with stirring, to 110° C. and held for 15 minutes before being cooled back down to 30° C. A second solution of bromotetralin (8.0 g) in 5 ml of diethyl ethylene glycol was now injected into the reaction vessel. The temperature was now raised to 105° C. and held for 72 hours with stirring under an argon blanket. The bromo and amino tetralins maybe the pure 1 or 2-tetralin isomer or isomer mixtures of the two. In this example, a mixture of 1 and 2-bromotetralin was used.

The reaction was then cooled to room temperature and diluted in 200 ml of hexanes to precipitate out any insoluble salts. This material was then filtered to remove any unwanted salts and the solution was concentrated down to 50 ml on a roto-evaporator. The hexane concentrate was passed through a silica gel column using hexane as the column solvent to isolate the tetralin product. The process of running a silica gel column may be repeated several times to isolate a pure product. The product was isolated as 3-4 grams of a yellow viscous liquid which may solidify on standing and melts above 40° C.

EXAMPLE 2

Preparation of Ditetralin Amine Using Palladium Coupling Catalyst

Into a 50 ml reaction vessel equipped with a mechanical stirrer, thermocouple, heating mantle and an argon blanket was charged powdered sodium t-butoxide (8.7 g, 0.087 mol). To this reaction vessel was now charged a dry argon degassed solution of bromotetralin (9.6 g, 0.045 mol), aminotetralin (7.4 g, 0.050 mol), tris(dibenzylideneacetone)dipalladium (0.18 g, 0.00020 mol) and RAC-2,2'-bis-(diphenylphosphino)-1,1'-bi-naphthyl (0.24 g, 0.00040 mol) in 25 ml of xylene. The reaction mixture was stirred vigorously under an argon atmosphere raising the temperature to 115° C. and holding these conditions for 20 hours. The reaction media was then cooled to room temperature and diluted with 100 ml of hexane and allowed to stand for one hour before being filtered. The filtered solution was then washed with 1×50 ml of 5% aqu. sodium hydroxide, 1×50 ml of 5% aqu. sodium bicarbonate and 1×50 ml of water, dried over anhydrous magnesium sulfate and filtered. The solution was concentrated to 75 ml and passed through a 50×50 mm chromatography column of silica gel using hexane as the column solvent. The hexane and xylene solvent was then stripped off under vacuum. The final product was a yellow-orange viscous liquid weighing 7.5 g.

EXAMPLE 3

Preparation of Ditetralin Amine Using Thermal Hot Tube Coupling over Solid Lewis Acid Catalyst Tetralin amine can be converted to di-tetralin amine using a process similar to the commercial process of converting aniline to diphenyl amine (DPA). This process involves converting tetralin amine to ditetralin amine by passing tetralin amine through a fixed bed reactor, in this example a ⅜'s inch glass tube, at 300-500° C. containing aluminum oxide or zeolite lewis acid pellet catalysts.

To hold the catalyst in a vertical glass tube, a half inch glass wool plug was inserted in the glass tube a little less than half way up the tube. The catalyst was then poured down the top of the tube to the desired amount. Crushed glass, 25-50 mesh, was then poured down the top of the tube to the desired amount. The crushed glass was also added on top of the catalyst to help maintain the tetralin amine in the gas phase before it comes in contact with the catalyst.

The glass tube containing a one inch loading of catalyst was placed vertically in the middle of the furnace. The top and bottom of the furnace was closed off with the ceramic tile plates by sliding the glass tube through the hole in the ceramic plates. On top of the glass tube was placed the "T" tube with septum to insert a steel syringe needle and nitrogen gas inlet.

The solid catalysts can be either used in the bead or pellet form or ground down to the 25-50 mesh size. The catalyst was first pre-conditioned with only the nitrogen gas connected to the top of the glass tube, the nitrogen flow was set at 55 ml/min through the tube. The furnace was now turned on and heated to 500-550° C. The temperature and nitrogen flow rate were maintained for 18 hours. After 18 hours, the temperature was reset to the temperature desired for the experiment to begin.

In this experiment, the catalyst used will be 25-50 mesh aluminum oxide and the furnace temperature will be set at 360° C. The syringe, pre-filled with tetralin amine, was connected to the syringe pump and the steel needle inserted in the top of the "T" tube septum far enough such that the tip of the needle was one inch above the entrance of the furnace. The nitrogen flow rate was now reset to 10-15 ml/min. for this experiment. The syringe pump flow rate was also set to 0.34 ml/hr for the tetralin amine injection rate. The syringe pump was now started. After several hours, a sample of the product exiting the bottom of the glass tube was taken and analyzed by gas chromatography (GC) and found to contain 3-4% ditetralin amine. The remainder of the product was mostly starting tetralin amine.

EXAMPLE 4

Preparation of SAE 10W-30 Motor Oil Formulation

To a motor oil formulation was blended 1 weight percent of the ditetralin amine of Example 1 to form a SAE 10W-30 motor oil formulation. The SAE 10W-30 motor oil formulation is set forth in Table 2.

TABLE 2

| SAE 10W-30 Motor Oil Formulation (Base Blend) | |
|---|---|
| | wt % |
| Solvent Neutral 100 | Balance |
| Overbased Calcium Sulfonate Detergent | 1.3 |
| Dispersant | 6.0 |
| Rust/Corrosion Inhibitor | 0.75 |
| Commercial or experimental Antioxidant | 1.0 |
| Pour Point Depressant | 0.1 |
| OCP VI Improver | 5.5 |
| ZDDP | 0.8 |

COMPARATIVE EXAMPLE A

Preparation of SAE 10W-30 Motor Oil Formulation

The SAE 10W-30 motor oil formulation set forth in Table 2 was prepared with no antioxidant added of any type.

COMPARATIVE EXAMPLE B

Preparation of SAE 10W-30 Motor Oil Formulation

To the SAE 10W-30 motor oil formulation set forth in Table 2 was blended 1 weight percent of alkylated diphenyl amine (commercially available as Naugalube 438L).

COMPARATIVE EXAMPLE C

Preparation of SAE 10W-30 Motor Oil Formulation

To the SAE 10W-30 motor oil formulation set forth in Table 2 was blended 1 weight percent of N'-alkylated N-phenylphenylenediamine (commercially available as Naugalube 420).

EXAMPLE 5

Preparation of a Turbine Oil Test Formulation

To a turbine oil formulation was blended 1 weight percent of the ditetralin amine of Example 1. The turbine oil formulation is set forth in Table 3.

TABLE 3

Turbine Reference Test Oil Composition

| Additive in Oil | Weight Percent in composition |
|---|---|
| Antioxidant or Experimental Invention | 1.00 wt. % |
| Corrosion Inhibitor | 0.05 wt. % |
| Defoamer | 0.005 wt. % |
| Metal Deactivator | 0.03 wt. % |
| Exxon 100LP | Balance |

COMPARATIVE EXAMPLE D

Preparation of a Turbine Oil Formulation

To the turbine oil formulation set forth in Table 3 was prepared with no antioxidant added of any type. 1.0 weight percent Exxon 100LP was used in place of the antioxidant dosage.

COMPARATIVE EXAMPLE E

Preparation of a Turbine Oil Formulation

To the turbine oil formulation set forth in Table 3 was blended 1 weight percent of the antioxidant alkylated diphenyl amine (commercially available as Naugalube 438L).

COMPARATIVE EXAMPLE F

Preparation of a Turbine Oil Formulation

To the turbine oil formulation set forth in Table 3 was blended 1 weight percent of antioxidant N'-alkylated N-phenylphenylenediamine (commercially available as Naugalube 420).

Testing

Each of the motor oil formulations of Example 4 and Comparative Examples A-C were evaluated using the Thermo-Oxidation Engine Oil Simulation Test (TEOST) and each of the turbine oil formulations of Example 5 and Comparative Examples D-F were evaluated using Rotary Bomb Oxidation Test (RBOT) as described below.

Mid-High Temperature Thermo-oxidative Engine Oil Simulation Test

The Mid-High Temperature Thermo-oxidative Engine Oil Simulation Test (MHT TEOST) was performed to determine the deposit forming tendencies of the motor engine oil. The improved thermal deposit control of the additives of this invention in stabilizing the engine oil formulation has been clearly demonstrated by the MHT TEOST. This test determines the mass of deposit formed on a specially constructed steel rod by continuously stressing a repetitive passage of 8.5 ml of test oil under thermal-oxidative and catalytic conditions. The instrument used was manufactured by Tannas Co. and has a typical repeatability of 0.15(x+16) mg wherein x is the mean of two or more repeated test results. The TEOST test conditions are listed in Table 4. The less the amount of deposits obtained, the better the oxidation stability of the oil.

The total amount of added antioxidant was 1.0 weight percent in each blend. The significantly lower amounts of deposits obtained for blend 2 as compared to commercial diphenylamine (Comp. Example B) and phenylenediamine (Comp. Example C), as shown in the data set forth in Table 5, demonstrate that the lubricating oil compositions containing the antioxidant of this invention have superior oxidative stability to produce smaller amounts of deposits in the TEOST.

TABLE 4

TEOST MHT Test Conditions

| Test Parameters | Settings |
|---|---|
| Test duration | 24 hours |
| Rod Temperature | 285° C. |
| Sample size | 8.5 g (mixture of 8.4 g of oil and 0.1 g of catalyst) |
| Sample flow rate | 0.25 g/min |
| Flow rate (dry air) | 10 mL/min |
| Catalyst | Oil soluble mixture containing Fe, Pb, and Sn |

TABLE 5

TEOST Results

| Ex./Comp. Ex. | mg deposits |
|---|---|
| Example 4 | 35 |
| Comp. Ex. A | 109 |
| Comp. Ex. B | 75 |
| Comp. Ex. C | 55 |

It can be seen from the above data that the addition of a diaromatic amine derivative additive of the present invention reduces the total deposit mass of the base blend formulation.

Rotating Pressure Vessel Oxidation Test

The Rotating Pressure Vessel Oxidation Test (RPVOT) was conducted according to the standard test method specified by ASTM D 2272-85. The test conditions are given in Table 6. The results of this test are set forth in Table 7. The time for a 25 psi pressure drop was 100 minutes for the Reference Oil. The longer the time to reach the endpoint indicates improved oxidative stability. The Turbine reference base oil composition used in the RBOT test is set forth in Table 3.

This test method utilizes an oxygen-pressured bomb to evaluate the oxidation stability of new and in service turbine oils having the same composition (base stock and additives) in the presence of water and a copper catalyst coil at 150° C. The test oil, water and a copper catalyst coil, contained in a covered glass container, are placed in a bomb equipped with a pressure gauge. The bomb is charged with oxygen to a pressure of 90 psi and placed in a constant temperature oil bath set at 150° C., and rotated axially at 100 rpm at an angle of 30 degrees from the horizontal. The number of minutes required to reach a specific drop in gage pressure (in this test for this invention, 25 psi) is the oxidation stability of the test sample.

TABLE 6

RPVOT Test Conditions

Initial Conditions

| Copper Catalyst Coil Weight | 55.6 grams |
|---|---|
| Sample Size Weight | 50.00 grams |
| Distilled Water weight | 5 grams |
| Temperature, C. | 150° C. |
| Oxygen Initial Pressure at RT | 90° C. |

TABLE 6-continued

RPVOT Test Conditions

Initial Conditions

| | |
|---|---|
| Oxygen Max Pressure at 150 C. | 188 psi |
| Pressure Drop to End Test | 25 psi |

TABLE 7

RPVOT Results

| Ex./Comp. Ex. | Time, minutes |
|---|---|
| Example 5 | 2913 |
| Comp. Ex. D | <100 |
| Comp. Ex. E | 718 |
| Comp. Ex. F | 766 |

It can be seen from the above data that the turbine oil formulation containing the diaromatic amine derivative additive of the present invention (Example 5) possessed significantly better oxidative stability than the turbine oil formulation of Comparative Examples D-F, which are outside the scope of the invention.

The synergistic effect from a combined use of a ditetralin amine of the present invention and a secondary diarylamine has been demonstrated in a 5W20 engine oil as set forth below.

EXAMPLE 6

Preparation of a 5W20 Engine Oil

The 5W20 engine oil formulation was pre-blended with the following commercially available components as set forth in Table 8. There is no particular restriction on the type and exact composition of the materials in the context of the present invention.

TABLE 8

5W20 Engine oil Pre-blend

| Component | wt % |
|---|---|
| Base oil, API Group II | Balance |
| Overbased Calcium Sulfonate Detergents | 2.5 |
| ZDDP | 0.5 |
| Succinimide Dispersant | 6.4 |
| Pour Point Depressant | 0.1 |
| OCP VI Improver | 5.0 |

To the 5W20 engine oil pre-blend set forth in Table 8, 0.8 weight percent of the ditetralin amine of Example 1 and 0.2 weight percent of a nonylated diphenylamine, commercially available as Naugalube 438L (Chemtura Corp.), were blended to form a fully formulated 5W20 engine oil.

EXAMPLE 7

Preparation of a 5W20 Engine Oil

To the 5W20 engine oil pre-blend set forth in Table 8 was blended 1.0 weight percent of the ditetralin amine of Example 1 to form a 5W20 engine oil.

COMPARATIVE EXAMPLE G

Preparation of a 5W20 Engine Oil

To the 5W20 engine oil pre-blend set forth in Table 8 was blended 1.0 weight percent of the Naugalube 438L to form a 5W20 engine oil.

Testing

The antioxidant performance of the engine oil formulations of Examples 6 and 7 and Comparative Example G was evaluated using the Thermal-oxidation Engine Oil Simulation Test (TEOST, ASTM D7097). The test conditions are given in Table 4.

Table 9 shows the TEOST test results. Both "actual deposits", as well as "expected deposits", calculated from weighted actual value of individual component (Example 7 for ditetralin amine; Comp. Example G for nonylated diphenylamine) are shown for the blend of Example 6. The significantly lower amount of deposits obtained for the blend of Example 6 relative to that of each individual antioxidant blend and to the expected value demonstrates that engine oils containing the ditetralin amine of this invention and an alkylated diphenylamine has superior oxidative stability to prevent deposit formation under high temperature oxidation conditions.

TABLE 9

TEOST Results

| Engine oil formulation | Actual deposits, mg | Expected deposits, mg |
|---|---|---|
| 5W20 Pre-blend | 132 | — |
| Example 6 | 17 | 41 |
| Example 7 | 37 | — |
| Comp. Example G | 55 | — |

The synergistic effect from a combined use of ditetralin amine of the present invention and a secondary diarylamine has been demonstrated in an industrial turbine oil tested by the RPVOT (ASTM D2272) method.

EXAMPLE 8

Preparation of a Turbine Oil Formulation

The turbine oil formulation was pre-blended with the following commercially available components set forth in Table 10. There is no particular restriction on the type and exact composition of the materials in the context of the present invention.

TABLE 10

Turbine Oil Formulation Pre-blend

| Component | wt % |
|---|---|
| Base oil, API Group II | Balance |
| Corrosion Inhibitor | 0.1 |
| Metal Deactivator | 0.1 |

To the turbine oil pre-blend set forth in Table 10, 0.4 weight percent of ditetralin amine of Example 1 and 0.1 weight percent of an nonylated diphenylamine, commercially available as the Naugalube 438L, were blended to form a turbine oil.

EXAMPLE 9

Preparation of a Turbine Oil Formulation

To the turbine oil pre-blend set forth in Table 10 was blended 0.5 weight percent of the ditetralin amine of Example 1 to form a turbine oil.

COMPARATIVE EXAMPLE H

Preparation of a Turbine Oil Formulation

To the turbine oil pre-blend set forth in Table 10 was blended 0.5 weight percent of the Naugalube 438L to form a turbine oil.

Testing

The RPVOT was conducted according to the ASTM standard method specified in D2272-02. The test conditions are given in Table 6.

Table 11 shows the RPVOT results. Both "actual time", as well as "expected time" calculated from weighted actual value of each individual component (Example 9 for the ditetralin amine; Comp. Example H for nonylated diphenylamine) are shown for the blend of Example 8. It can be seen from the data that the turbine oil formulation of Example 8 containing the ditetralin amine of the present invention and alkylated diphenylamine possessed significantly better oxidative stability by exhibiting longer oxidation induction time than those the turbine oil formulations of Example 9 and Comparative Example H and the expected value.

TABLE 11

RPVOT Oxidation Induction Time

| Turbine oil formulation | Actual time, min. | Expected time, min. |
|---|---|---|
| Turbine Oil Pre-blend | 37 | — |
| Example 8 | 3155 | 2522 |
| Example 9 | 2989 | — |
| Comp. Example H | 653 | — |

The synergistic effect from a combined use of ditetralin amine of the present invention and a sulfurized phenolic antioxidant has been demonstrated in a 5W20 engine oil.

EXAMPLE 10

Preparation of 5W20 Engine Oil

To the 5W20 engine oil pre-blend set forth in Table 8, 0.8 weight percent of the ditetralin amine of Example 1 and 0.2 weight percent of a 4,4-thiobis(2-tert-butyl-5-methylphenol), commercially available as the Naugalube 18 (Chemtura Corp.), were blended to form a 5W20 engine oil.

EXAMPLE 11

Preparation of 5W20 Engine Oil

To the 5W20 engine oil pre-blend set forth in Table 8 was blended 1.0 weight percent of the ditetralin amine of Example 1 to form a 5W20 engine oil.

COMPARATIVE EXAMPLE I

Preparation of 5W20 Engine Oil

To the 5W20 engine oil pre-blend set forth in Table 8 was blended 1.0 weight percent of the Naugalube 18 to form a 5W20 engine oil.
Testing The antioxidant performance of the engine oil formulations of Examples 10 and 11 and Comparative Example I was evaluated using the TEOST (ASTM D7097). The test conditions are given in Table 4.

Table 12 shows the TEOST test results. Both "actual deposits", as well as "expected deposits", calculated from weighted actual value of individual component (Example 11 for the ditetralin amine; Comp. Example I for Naugalube 18) are shown for the blend of Example 10. The lower amount of deposits obtained for the blend of Example 10 relative to that of each individual antioxidant blend and to the expected value demonstrates that engine oils containing the ditetralin amine of this invention and sulfurized hindered phenolic has superior oxidative stability to prevent deposit formation under high temperature oxidation conditions.

TABLE 12

TEOST Results

| Engine oil formulation | Actual deposits, mg | Expected deposits, mg |
|---|---|---|
| 5W20 Engine Oil Pre-blend | 132 | — |
| Example 10 | 22 | 36 |
| Example 11 | 37 | — |
| Comp. Example I | 34 | — |

The synergistic effect from a combined use of the ditetralin amine of the present invention and a sulfurized phenolic antioxidant has been demonstrated in an industrial turbine oil tested by the RPVOT (ASTM D2272) method.

EXAMPLE 12

Preparation of a Turbine Oil Formulation

To the turbine oil pre-blend set forth in Table 10, 0.4 weight percent of the ditetralin amine of Example 1 and 0.1 weight percent of a 4,4-thiobis(2-tert-butyl-5-methylphenol), commercially available as the Naugalube 18, were blended to form a turbine oil.

EXAMPLE 13

Preparation of a Turbine Oil Formulation

To the turbine oil pre-blend set forth in Table 10 was blended 0.5 weight percent of the ditetralin amine of Example 1 to form a turbine oil.

COMPARATIVE EXAMPLE J

Preparation of a Turbine Oil Formulation

To the turbine oil pre-blend set forth in Table 10 was blended 0.5 weight percent of the Naugalube 18 to form a turbine oil.
Testing The RPVOT was conducted according to the ASTM standard method specified in D2272-02. The test conditions are given in Table 6.

Table 13 shows the RPVOT results. Both "actual time", as well as "expected time" calculated from weighted actual value of each individual component (Example 13 for the ditetralin amine; Comp. Example J for the Naugalube 18) are shown for the blend of Example 12. It can be seen from the data that the turbine oil of Example 12 containing the ditetralin amine of the present invention and sulfurized phenolic antioxidant exhibited longer oxidation induction time to the "expected value".

TABLE 13

RPVOT Oxidation Induction Time

| Turbine oil formulation | Actual time, min. | Expected time, min. |
|---|---|---|
| Example 12 | 2707 | 2496 |
| Example 13 | 2989 | — |
| Comp. Example J | 524 | — |

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. An isomeric mixture comprising diaromatic amine compounds of the general formula:

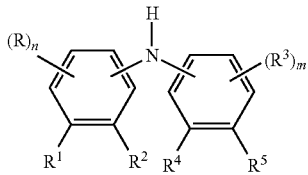

wherein n is from 0 to 3; m is from 0 to 3;

each R and $R^3$ substituent is independently hydrogen, a straight or branched $C_1$-$C_{32}$ alkyl group or alkenyl group, substituted or unsubstituted $C_3$-$C_{12}$ cycloalkyl, substituted or unsubstituted $C_5$-$C_{12}$ aryl, hydroxyl-containing group, halogen, substituted or unsubstituted $C_1$-$C_{20}$ alkoxy, ester-containing group, ether-containing group, polyether-containing group, amide-containing group, or amine-containing group or two R substituents and/or two $R^3$ substituents together with the carbon atom to which they are bonded are joined together to form a substituted or unsubstituted, saturated, partially saturated or unsaturated $C_5$-$C_{30}$ ring structure optionally containing one or more heteroatoms;

$R^1$ and $R^2$ together with the carbon atom to which they are bonded are joined together to form a substituted or unsubstituted, saturated or partially saturated $C_5$-$C_{30}$ ring structure optionally containing one or more heteroatoms, and $R^4$ and $R^5$ together with the carbon atom to which they are bonded are joined together to form a substituted or unsubstituted, saturated or partially saturated $C_5$-$C_{30}$ ring structure optionally containing one or more heteroatoms.

2. The isomeric mixture of claim 1, wherein for each isomer of the diaromatic amine compound R and $R^3$ are hydrogen and $R^1$ and $R^2$ together with the carbon atom to which they are bonded, and $R^4$ and $R^5$ together with the carbon atom to which they are bonded are joined together to form a substituted or unsubstituted, saturated or partially saturated 5-, 6-, or 7-membered ring optionally substituted with one or more heteroatoms.

3. The isomeric mixture of claim 1, comprising a 1,1-isomer or 1,2-isomer or 2,2-isomer or mixtures thereof of the diaromatic amine compound.

4. The isomeric mixture of claim 1, comprising a 1,1-isomer and 1,2-isomer of the diaromatic amine compound.

5. The isomeric mixture of claim 1, comprising a 1,1-isomer and 2,2-isomer of the diaromatic amine compound.

6. The isomeric mixture of claim 1, comprising a 1,2-isomer and 2,2-isomer of the diaromatic amine compound.

7. A lubricating oil composition comprising (a) at least one oil of lubricating viscosity and (b) an effective amount of an isomeric mixture of claim 1.

8. The lubricating oil composition of claim 7, wherein the at least one oil of lubricating viscosity is selected from the group consisting of engine oils, transmission fluids, hydraulic fluids, gear oils, marine cylinder oils, compressor oils, refrigeration lubricants and mixtures thereof.

9. The lubricating oil composition of claim 7, wherein the at least one oil of lubricating viscosity has a viscosity of about 1.5 to about 2000 centistokes (cSt) at 100° C.

10. The lubricating oil composition of claim 7, further comprising at least one lubricating oil additive.

11. The lubricating oil composition of claim 7, further comprising at least one lubricating oil additive selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

12. The lubricating oil composition of claim 7, further comprising at least one lubricating oil additive selected from the group consisting of an alkylated diphenylamine, alkylated hindered phenolic, alkylated substituted or unsubstituted phenylenediamine, arylated substituted or unsubstituted phenylenediamine, alkylated oil soluble copper compound, alkylated sulfur containing compound known to impart oxidation stability and mixtures thereof.

13. The lubricating oil composition of claim 12, wherein the alkylated sulfur containing compound known to impart oxidation stability is selected from the group consisting of a phenothiazine, sulfurized olefin, thiocarbamate, sulfur bearing hindered phenolic, zinc dialkyldithiophosphate and mixtures thereof.

14. The lubricating oil composition of claim 7, further comprising at least one lubricating oil additive selected from the group consisting of a fatty acid ester or amide, organo molybdenum compound, molybdenum dialkyldithiocarbamate, molybdenum dialkyl dithiophosphate, molybdenum disulfide, tri-molybdenum cluster dialkyldithiocarbamate, non-sulfur molybdenum compound and mixtures thereof.

15. The lubricating oil composition of claim 7, further comprising at least one lubricating oil additive selected from the group consisting of a zinc dialkyldithiophosphate, zinc diaryldithiophosphate, dialkyldithiophosphate ester, diaryl dithiophosphate ester and mixtures thereof.

16. The lubricating oil composition of claim 7, having a phosphorous content of less than about 0.08 weight percent.

17. An additive package comprising about 1 to about 75 weight percent of the isomeric mixture of claim 1.

18. An additive package comprising about 1 to about 75 weight percent of the isomeric mixture of claim 1 and at least one other lubricating oil additive.

19. The additive package of claim 18, wherein the at least one other lubricating oil additive is selected from the group consisting of an alkylated diphenylamine, alkylated hindered phenolic, alkylated substituted or unsubstituted phenylenediamine, alkylated oil soluble copper compound, alkylated sulfur containing compound known to impart oxidation stability and mixtures thereof.

20. The additive package of claim 18, wherein the alkylated sulfur containing compound known to impart oxidation stability is selected from the group consisting of phenothiazine, sulfurized olefin, thiocarbamate, sulfur bearing hindered phenolic, zinc dialkyldithiophosphate and mixtures thereof.

21. The additive package of claim 18, wherein the at least one other lubricating oil additive is selected from the group consisting of a fatty acid ester or amide, organo molybdenum compound, molybdenum dialkyldithiocarbamate, molybdenum dialkyl dithiophosphate, molybdenum disulfide, tri-molybdenum cluster dialkyldithiocarbamate, non-sulfur molybdenum compound and mixtures thereof.

22. The additive package of claim 18, wherein the at least one other lubricating oil additive is selected from the group consisting of a zinc dialkyldithiophosphate, zinc diaryldithiophosphate, dialkyldithiophosphate ester, diaryl dithiophosphate ester and mixtures thereof.

23. A stabilizer-containing composition comprising (a) an organic material subject to oxidative, thermal, and/or light-induced degradation and in need of stabilization to prevent or inhibit such degradation; and (b) a stabilization effective amount of the isomeric mixture of claim 1.

24. The stabilizer-containing composition of claim 23, wherein the organic material is a natural or synthetic polymer.

25. The stabilizer-containing composition of claim 23, wherein the organic material is selected from the group consisting of a polyol, urethane, reaction product of a polyol and urethane, plastic, grease, roof sheeting, motor oil, cable, gasket, seal, compounded tire and rubber belt.

26. A method for stabilizing an organic material subject to oxidative, thermal, and/or light-induced degradation and in need of stabilization to prevent or inhibit such degradation, the method comprising adding to the organic material a stabilizing amount of the isomeric mixture of claim 1.

* * * * *